United States Patent [19]
Nickerson

[11] Patent Number: 4,892,654
[45] Date of Patent: Jan. 9, 1990

[54] TRAPPING ASSEMBLY

[76] Inventor: Mark A. Nickerson, 19 Glenlock Dr., Landenberg, Pa. 19350

[21] Appl. No.: 324,353

[22] Filed: Mar. 15, 1989

[51] Int. Cl.$^4$ ............................................. B01D 15/08
[52] U.S. Cl. ................................. 210/198.2; 210/659; 55/386
[58] Field of Search ............ 210/635, 656, 659, 198.2; 55/67, 386

[56]      References Cited
U.S. PATENT DOCUMENTS

| | | | |
|---|---|---|---|
| 3,510,271 | 5/1970 | Emneus | 210/198.2 |
| 4,348,131 | 8/1982 | Brownlee | 210/198.2 |
| 4,500,432 | 2/1985 | Poole | 210/659 |
| 4,597,866 | 7/1986 | Couillard | 210/198.2 |
| 4,636,315 | 1/1987 | Allen | 210/198.2 |
| 4,806,250 | 2/1989 | Takata | 210/198.2 |

OTHER PUBLICATIONS

Giddings, "High Pressure Gas Chromatography of Nonvolatile Species", Science (Oct. 4, 1968), pp. 67–73.
"Direct Coupling of a Dense (Supercritical) Gas Chromatograph to Mass Spectrometer using a Supersonic Molecular Beam Interface", Rev. Sci. Instrum. 52(9), Sep. 1981, pp. 1283–1295.
Tescom Corporation Sales Brochure 26–1600 and 26–1700, (publication date unknown & unavailable), Single Page References.
Union Molycorp "Lathologyy" advertisement, (publication data unknown & unavailable), single page reference.

Primary Examiner—Ernest G. Therkorn

[57]     ABSTRACT

Disclosed is a chromatographic trapping assembly suitable for use with supercritical fluids. The apparatus includes means suitable for electronic control of the expansion of pressurized fluid through an orifice into a fluid trapping assembly using an axially movable column to regulate fluid through the orifice.

4 Claims, 1 Drawing Sheet

TRAPPING ASSEMBLY

BACKGROUND OF THE INVENTION

This invention relates to trapping assemblies and to valve means suitable for use with such assemblies as part of the process for introducing trapped solutes into instruments such as gas, liquid or supercritical fluid chromatographs that are used to measure amounts of such solutes.

The use of gas, liquid and supercritical fluid chromatographs (hereinafter collectively referred to as "chromatographs") have long been used to measure amounts of solutes in fluids. In a gas chromatograph the carrier fluid is gas, e.g., nitrogen, and in a liquid chromatograph it is a liquid, e.g., methyl alcohol. In SFC chromatographs the carrier fluid is ordinarily a gas, e.g., $CO_2$, which is densified with increased pressure above its critical point. The density and thus the effective solvent power of a supercritical fluid can be controlled by pressure.

It has become increasingly important to be able to measure very small, even trace, amounts of solutes in a carrier fluid. This is particularly desirable in measuring very small amounts of contaminants, such as organic chemicals, pesticides, etc., in drinking water or foods in amounts of the order of 1 ppb. In such circumstances, the amount of solute may be below the minimum detectable quantity (MDQ) for most chromatographs.

In the method and apparatus of Poole et al., U.S. Pat. No. 4,500,432, granted Feb. 19, 1985 there is provided a way to concentrate solutes contained in fluids before they are applied to chromatographs for analysis. In general, the technique of Poole et al. involves concentrating a solute by passing a solvent containing it through a first trapping means (e.g., a packed column) that adsorbs the solute and passes the solvent to waste, passing a fluid (e.g., a supercritical fluid) through the first trapping means to dissolve or solubilize the solute therefrom and carry it into a second trapping means, and reducing the solubility parameter of the fluid in the second trapping means. Where a supercritical fluid carries the solute, the last step can involve passing the fluid from a high pressure to a much lower pressure. This permits the fluid to escape from the second trapping means leaving the solute concentrated therein. The second trapping means can be used by itself when a vessel containing a range of materials (solids, semi-solids, liquids dispersed as a stationary phase) replaces the first trapping means.

Currently known approaches to achieve pressure drops from high pressure systems to lower pressures include: (a) static orifices which are typically holes of about 3 to 20 microns in diameter in thin metal foil or at the end of converging ducts, or (b) lengths of capillary tubing (e.g., 20 to 50 microns ID). Neither of the foregoing decouple control of pressure (and therefore density) from linear flow rate.

Often in larger systems (e.g., small pilot plant scale), conventional needle valves are used for pressure drop. These tend to suffer from large inaccessible volumes (dead volume) and inappropriately placed boundaries to the expanding stream so that sampling of high pressure fluid is not representative. Large valves also tend to suffer from poor design in getting sufficient heat into the device to balance heat lost during expansion and, thus, tend to "ice up" causing erratic flow or stoppages. Available back pressure regulators, using manually set, springdriven control pistons, do not contain nozzle geometry for sampling with the capability of electronic control of the pressure.

SUMMARY OF THE INVENTION

This invention provides a trapping assembly especially useful in the apparatus and method of the type described in Poole et al. since it largely overcomes the disadvantages or shortcomings of known fluid trapping assemblies suitable for use with supercritical fluids. This is accomplished by means suitable for electronic control of the expansion of pressurized fluid through an orifice into a fluid trapping assembly using an axially movable column to regulate fluid flow through the orifice. This invention is more particularly pointed out in the appended claims and is described in its preferred embodiments in the accompanying drawings and the detailed description thereof.

DETAILED DESCRIPTION OF THE INVENTION

Figure 1:
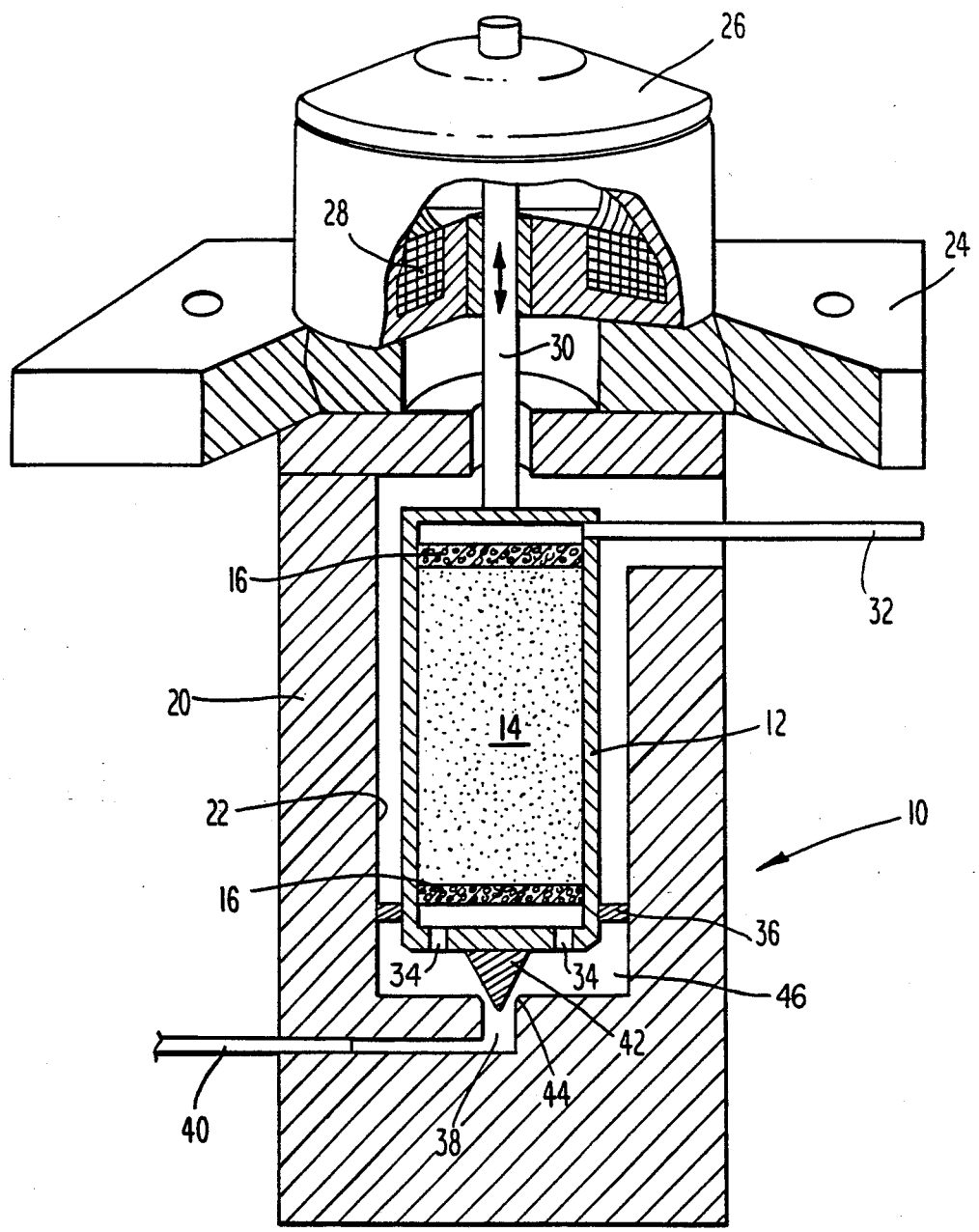
FIG. 1 is a partial cross-section of a semi-schematic view of a fluid trapping assembly and valve in accordance with this invention.

Referring now to the drawings, trapping assembly 10 contains a column 12 which is filled with packing material 14. Suitable packing material includes a wide variety of materials, e.g., metal cylinders, beads, spheres or particles which can suitably be made of stainless steel, nickel, nickel-copper, nickel chrome, cobalt chrome, etc. Other packing materials are glass or resin beads, particles, etc., sintered porous metal matrix of irregular or spherical metal, or silica or bonded-phase silica and polymeric particles, beads, etc. It is also possible that the column can be unpacked and have an interior coating of a polymer such as are known in the art of chromatography.

The column 12 is provided at top and bottom with suitable layers of frit 16 and 18 which can be a porous layer of stainless steel particles.

The column 12 is shown within cavity 22 in housing 20 which may be provided with a electric heating element and thermocouple not shown. At the top of housing 20 is plate 24. Mounted atop plate 24 is solenoid 26 shown partially cut away in FIG. 1 revealing windings 28 and axially moving shaft 30 reactive to the electric current flowing in the solenoid 26. Shaft 30 may be suitably attached at its lower end to the top of column 12 to engage said column and move it axially.

Column 12 is provided near its top with a fluid outlet tube 32, and near its base with one or more fluid inlet openings 34. A column seal 36 is firmly secured to the interior of cavity 22 and surrounds said column 12 in sealing engagement. Seal 36 may be mounted so as to permit column 12 to slide within it. Alternatively, seal 36 may be firmly attached to the column surface but permit movement of the column without breaking the attachment by flexibility and/or stretchability of seal 36. Since the actual distance of column axial movement is small, this may easily be accomplished by one skilled in the art.

At the bottom of cavity 22 is a fluid inlet orifice 38 for admitting fluid under high pressure from inlet tube 40. A conical projection 42 is attached to the base of column 12 to engage the upper end of orifice 38 and to form a valve seat 44. The materials of construction of said projection 42 and seat 44 should be selected so as to provide good sealing engagement without permitting high pressure fluids to force their way through seat 44 when closed. It is preferred that the cone-angle of projection 42 range from about 30 to 120 degrees. An angle of 60 degrees is satisfactory.

The material of construction of seal 36 can be selected from known materials, e.g., VESPEL polyimides, KALREZ fluorocarbons, or a flexible metal or polymeric diaphragm. Means for its attachment to cavity 22 and surrounding column 12 are well within the capabilities of those skilled in the art.

Electrical actuation of solenoid 26 provides axial movement to shaft 30 against column 12. When shaft 30 moves downward, projection 42 seals orifice 38. When fluid under pressure flows into inlet tube 40, pressure is exerted in orifice 38 and on projection 42. Fluid pressures between 1000 and 6000 psi are typical. If the pressure is sufficient, projection 42 is lifted from orifice 38 and a fluid passage is formed. The pressure required to lift projection 42 will depend upon the design of the orifice and the projection, as well as the downward pressure exerted by column 12 and solenoid 26. The seal 36 seals off the high pressure fluid from ambient pressure regions within the apparatus. The fluid passing through orifice 38 passes through openings 34 into column 12 to a region of lower pressure. If the fluid is a gas, e.g., carbon dioxide, held at temperatures and pressures above its critical point, the high density thereof increases its solubility parameter for the dissolved solute therein. When the fluid passes into the column 12 at a much lower pressure, the solute comes out of solution and is removed and collected (which includes being adsorbed, or otherwise retained on the packing within the column). The fluid, e.g., carbon dioxide at lower pressure can be removed from the column through outlet tube 32.

Thereafter, the column can be flushed by introducing fluid through tube 32 and removing it through tube 40, or the direction of flow can be reversed if desired.

The apparatus of this invention is especially useful in supercritical fluid trapping means described herein and especially for use in the invention of Poole et al. U.S. Pat. No. 4,500,432, the teachings of which are incorporated herein by reference. Such apparatus is, however, useful in any device where high pressure fluids are to be directed through a variable orifice into a column at a region of lower pressure, and which is to be operated by electronic control (e.g., the connection between the outlet of supercritical fluid chromatograph column and a detection means).

The axial movement illustrated herein is actuated by solenoid means; however, such devices can be also be axially driven by linear motors, piezo electric or magnetostrictive linear movement devices, and electrically actuated, thermally expanded linear movement devices. A function which can be achieved in accordance with this invention is the expansion of fluids and fluid mixtures from high pressures to low pressures where the range of fluids and mixtures includes supercritical fluids, nearly critical fluids, subcritical fluids, gases and liquids. Devices of this invention may be used to maintain or control pressure and/or to sample fluid from extraction devices, chromatographs, or fluid reservoirs.

I claim:

1. In a fluid trapping assembly for use with fluid systems having a column for removing and collecting a solute component of said fluid, the combination comprising:
   a fluid entrance located near the base of said column and a fluid outlet located near the top of said column,
   a valve chamber surrounding the base of said column having a fluid inlet orifice for admitting fluid into said chamber,
   a column seal surrounding said column and forming the upper part of said chamber, said seal being in sealing engagement with said column,
   orifice engagement means attached to the base of said column adapted to engage said fluid inlet orifice and restrict the flow of fluid into said chamber and through said column,
   axial movement means adapted to engage said column and move said orifice engagement means into and out of engagement with said orifice.

2. The assembly as defined in claim 1 wherein said axial movement means is driven by a solenoid.

3. The assembly as defined in claim 1 wherein said orifice engagement means is a conical projection extending from the base of said column.

4. The assembly as defined in claim 3 wherein the angel of the cone of said conical projection is between about 30 and 120 degrees.

* * * * *